(12) United States Patent
Hsiao et al.

(10) Patent No.: US 8,834,385 B2
(45) Date of Patent: Sep. 16, 2014

(54) METHOD FOR EXTRACTING THE FEATURE OF AN ABDOMINAL BREATHING AND A SYSTEM USING THE SAME

(75) Inventors: Tzu-Chien Hsiao, Hsinchu (TW); Ju-Hsin Hsu, Toufen Township, Miaoli County (TW)

(73) Assignee: National Chiao Tung University, Hsinchu (TW)

( * ) Notice: Subject to any disclaimer, the term of this patent is extended or adjusted under 35 U.S.C. 154(b) by 521 days.

(21) Appl. No.: 13/204,956

(22) Filed: Aug. 8, 2011

(65) Prior Publication Data

US 2013/0041277 A1 Feb. 14, 2013

(51) Int. Cl.
*A61B 5/08* (2006.01)
*A61B 5/113* (2006.01)
*G06F 19/00* (2011.01)

(52) U.S. Cl.
CPC .............. *A61B 5/0816* (2013.01); *A61B 5/113* (2013.01); *A61B 5/1135* (2013.01); *A61B 5/662* (2013.01); *A61B 5/08* (2013.01); *G06F 19/3437* (2013.01)
USPC ........................................ 600/529; 600/534

(58) Field of Classification Search
CPC ...... A61B 5/08; A61B 5/0806; A61B 5/0809; A61B 5/0816; A61B 5/0826; A61B 5/085; A61B 5/087; A61B 5/113; A61B 5/1135
USPC .......... 600/529, 533, 534, 535, 536, 537, 538
See application file for complete search history.

(56) References Cited

U.S. PATENT DOCUMENTS

| | | | | |
|---|---|---|---|---|
| 6,241,683 | B1 * | 6/2001 | Macklem et al. | 600/529 |
| 6,893,404 | B2 * | 5/2005 | Ragnarsdottir | 600/534 |
| 7,041,062 | B2 * | 5/2006 | Friedrichs et al. | 600/534 |
| 7,343,198 | B2 * | 3/2008 | Behbehani et al. | 600/509 |
| 7,801,593 | B2 * | 9/2010 | Behbehani et al. | 600/509 |
| 8,454,528 | B2 * | 6/2013 | Yuen et al. | 600/534 |
| 2006/0041201 | A1 * | 2/2006 | Behbehani et al. | 600/521 |
| 2007/0032733 | A1 * | 2/2007 | Burton | 600/509 |
| 2008/0319326 | A1 * | 12/2008 | Behbehani et al. | 600/484 |
| 2010/0130873 | A1 * | 5/2010 | Yuen et al. | 600/484 |
| 2010/0152600 | A1 * | 6/2010 | Droitcour et al. | 600/534 |
| 2010/0204601 | A1 * | 8/2010 | Masuo | 600/536 |
| 2010/0240999 | A1 * | 9/2010 | Droitcour et al. | 600/453 |
| 2010/0249630 | A1 * | 9/2010 | Droitcour et al. | 600/529 |
| 2010/0249633 | A1 * | 9/2010 | Droitcour et al. | 600/534 |
| 2010/0292568 | A1 * | 11/2010 | Droitcour et al. | 600/425 |

* cited by examiner

*Primary Examiner* — Navin Natnithithadha
(74) *Attorney, Agent, or Firm* — Muncy, Geissler, Olds & Lowe, P.C.

(57) ABSTRACT

A method for extracting the feature of an abdominal breathing is disclosed, capable of extracting the feature of an abdominal breathing, without the requirement of a standard model of an abdominal breathing and the execution of a learning process being executed prior to the method for extracting the feature of an abdominal breathing. By means of computing a plurality of intrinsic mode functions corresponding to the abdominal breathing signal received, an Euler angle function and an instantaneous frequency function of each of the plurality of intrinsic mode functions, and comparing the plurality of instantaneous frequency function with a pre-determined zero-point threshold region, the method for extracting the feature of an abdominal breathing defines one of the plurality of instantaneous frequency function as an abdominal breathing feature function, which contains the feature of the abdominal breathing. In this way, the feature of an abdominal breathing is extracted.

16 Claims, 11 Drawing Sheets

METHOD FOR EXTRACTING THE FEATURE OF AN ABDOMINAL BREATHING AND A SYSTEM USING THE SAME

BACKGROUND OF THE INVENTION

1. Field of the Invention

The present invention relates to a method for extracting the feature of an abdominal breathing and an abdominal breathing feature extracting system, more particularly, to the method for extracting the feature of an abdominal breathing and the abdominal breathing feature extracting system capable of extracting the feature of an abdominal breathing, without the requirement of a standard model of an abdominal breathing and the execution of a learning process, which is executed prior to the method for extracting the feature of an abdominal breathing, letting the person to learn how to execute a standard abdominal breathing.

2. Description of Related Art

In recent years, abdominal breathing plays an important role in rehabilitation and stress-released procedure. However, a person who needs to execute an abdominal breathing, such as a patient going to have a heart surgery, must be trained for a period of time by a teacher, such as a doctor, or a nurse. Besides, the results of the training, such as the correctness of the execution of the abdominal breathing, is not yet able to evaluated efficiently, as a standard model of an abdominal breathing is still required for the person to learn with. Moreover, the standard model is not necessarily suitable for full spectrum of people, such as from a children to an elderly.

As mentioned above, a learning process must be executed, for the person to learn with the standard model, which will cost a lot of time, and a certain level of cost. And most important of all, the person must be the same place with the teacher teaching the abdominal breathing, raising a lot of difficulty for the person in transportation, especially for the elderly.

As a result, a method for extracting the feature of an abdominal breathing and an abdominal breathing feature extracting system capable of extracting the feature of an abdominal breathing, without the requirement of a standard model of an abdominal breathing and the execution of a learning process, which is executed prior to the method for extracting the feature of an abdominal breathing, letting the person to learn how to execute a standard abdominal breathing.

SUMMARY OF THE INVENTION

It is one object of the present invention is to provide a method for extracting the feature of an abdominal breathing, capable of extracting the feature of an abdominal breathing, without the requirement of a standard model of an abdominal breathing and the execution of a learning process being executed prior to the method for extracting the feature of an abdominal breathing.

It is another object of the present invention is to provide an abdominal breathing feature extracting system, capable of extracting the feature of an abdominal breathing, without the requirement of a standard model of an abdominal breathing and the execution of a learning process being executed prior to the method for extracting the feature of an abdominal breathing.

To achieve the object, the method for extracting the feature of an abdominal breathing of the present invention comprises the following steps of: receiving an abdominal breathing signal; executing an empirical mode decomposition process on the abdominal breathing signal, for computing a plurality of intrinsic mode functions; basing on the plurality of intrinsic mode functions and the results obtained after the execution of a Hilbert transform on the plurality of intrinsic mode functions, computing an Euler angle function of each of the plurality of intrinsic mode functions; taking the partial derivative of the Euler angle function of each of the plurality of intrinsic mode functions, with respect to time, for computing an instantaneous frequency function of each of the plurality of intrinsic mode functions, and extracting a plurality of maximum values of each of the plurality of instantaneous frequency functions; and according to a pre-determined sequence, comparing the plurality of maximum values of each of the plurality of instantaneous frequency functions with a zero-point threshold region, respectively, and when a result that all of the plurality of maximum values of one of the plurality of instantaneous frequency functions falling into the zero-point threshold region is obtained, the instantaneous frequency function having the plurality of maximum values is defined as an abdominal breathing feature function.

To achieve the object, the abdominal breathing feature extracting system of the present invention comprises: a sensing module, for sensing an abdominal breathing signal; a computing module, coupled with the sensing module, for extracting an abdominal breathing feature function; and an abdominal breathing feature output module, coupled with the computing module, for outputting the abdominal breathing feature function; wherein, the computing module extracts the abdominal breathing feature function from the abdominal breathing signal by means of executing an abdominal breathing feature extracting method, and the abdominal breathing feature extracting method comprises the following steps of: receiving the abdominal breathing signal; executing an empirical mode decomposition process on the abdominal breathing signal, for computing a plurality of intrinsic mode functions; basing on the plurality of intrinsic mode functions and the results obtained after the execution of a Hilbert transform on the plurality of intrinsic mode functions, computing an Euler angle function of each of the plurality of intrinsic mode functions; taking the partial derivative of the Euler angle function of each of the plurality of intrinsic mode functions, with respect to time, for computing an instantaneous frequency function of each of the plurality of intrinsic mode functions, and extracting a plurality of maximum values of each of the plurality of instantaneous frequency functions; and according to a pre-determined sequence, comparing the plurality of maximum values of each of the plurality of instantaneous frequency functions with a zero-point threshold region, respectively, and when a result that all of the plurality of maximum values of one of the plurality of instantaneous frequency functions falling into the zero-point threshold region is obtained, the instantaneous frequency function having the plurality of maximum values is defined as the abdominal breathing feature function.

Since the method for extracting the feature of an abdominal breathing can compute a plurality of intrinsic mode functions corresponding to an abdominal breathing signal received, and then compute an Euler angle function of each of the plurality of intrinsic mode functions. Later, an instantaneous frequency function of each of the plurality of intrinsic mode functions can be compute by taking the partial derivative of the Euler angle function of each of the plurality of intrinsic mode functions, with respect to time. Then, a plurality of maximum values of each of the plurality of instantaneous frequency functions can be extracted and compared with a zero-point threshold region. At final, with respect to the result of the comparison, an abdominal breathing feature function corresponding to the abdominal breathing signal received can be defined. Therefore, the method for extracting the feature of an abdominal breathing of the present invention is capable of extracting the feature of an abdominal breathing directly from the abdominal breathing signal received, without the requirement of a standard model of an abdominal breathing and the execution of a learning process being executed prior to the method for extracting the feature of an abdominal breathing.

In addition, by including an computing module executing the method for extracting the feature of an abdominal breathing, a sensing module used for receiving the abdominal breathing signal, and an abdominal breathing feature output module used for outputting the abdominal breathing feature function, the abdominal breathing feature extracting system of the present invention is capable of extracting the feature of an abdominal breathing, without the requirement of a standard model of an abdominal breathing and the execution of a learning process being executed prior to the method for extracting the feature of an abdominal breathing.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
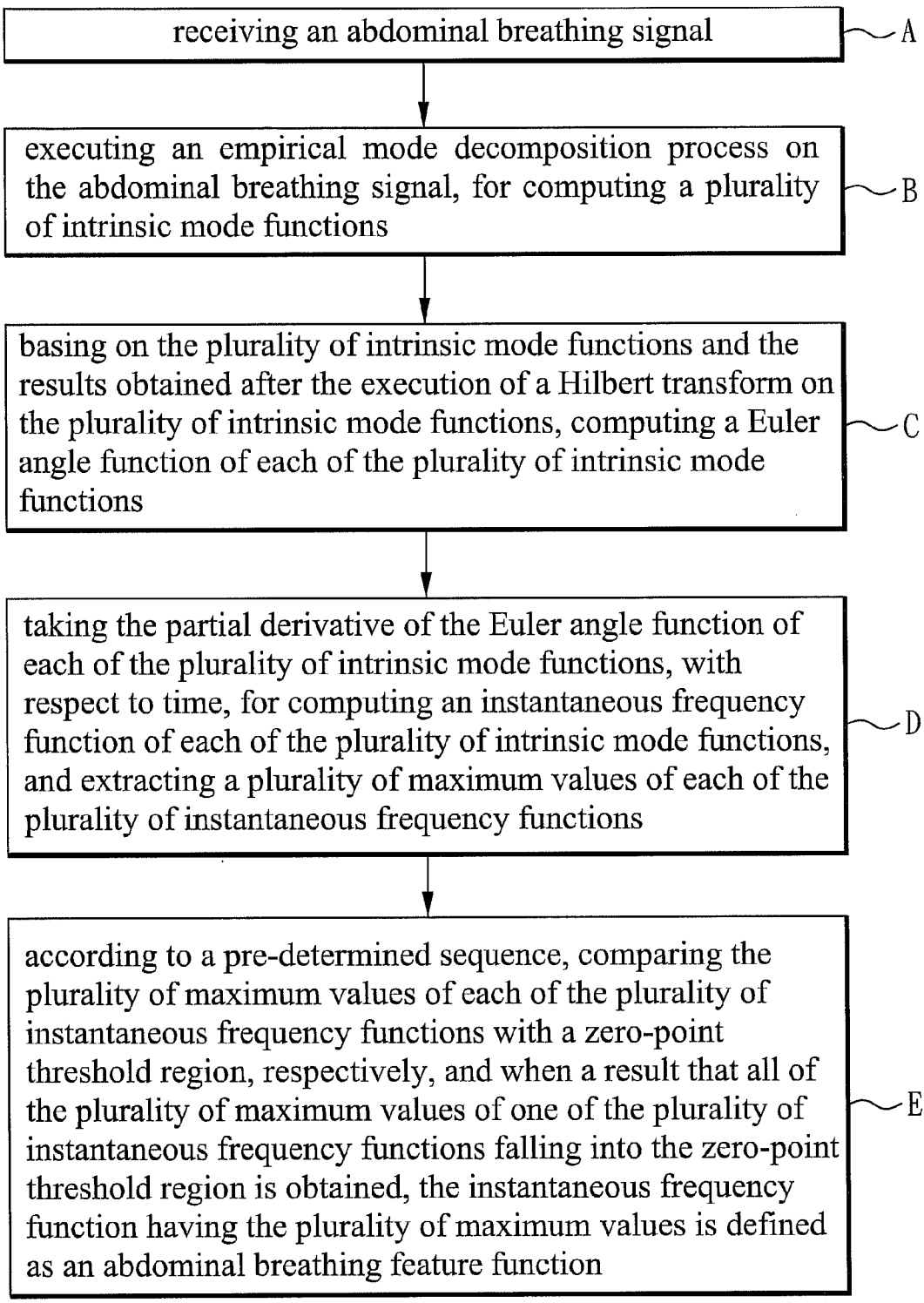
FIG. 1 is a flowchart of the method for extracting the feature of an abdominal breathing according to first embodiment of the present invention.

As shown in FIG. 1, which is a flowchart of the method for extracting the feature of an abdominal breathing according to first embodiment of the present invention, the method for extracting the feature of an abdominal breathing comprises the following steps of:

(A) receiving an abdominal breathing signal;

(B) executing an empirical mode decomposition process on the abdominal breathing signal, for computing a plurality of intrinsic mode functions;

(C) basing on the plurality of intrinsic mode functions and the results obtained after the execution of a Hilbert transform on the plurality of intrinsic mode functions, computing an Euler angle function of each of the plurality of intrinsic mode functions;

(D) taking the partial derivative of the Euler angle function of each of the plurality of intrinsic mode functions, with respect to time, for computing an instantaneous frequency function of each of the plurality of intrinsic mode functions, and extracting a plurality of maximum values of each of the plurality of instantaneous frequency functions; and (E) according to a pre-determined sequence, comparing the plurality of maximum values of each of the plurality of instantaneous frequency functions with a zero-point threshold region, respectively, and when a result that all of the plurality of maximum values of one of the plurality of instantaneous frequency functions falling into the zero-point threshold region is obtained, the instantaneous frequency function having the plurality of maximum values is defined as an abdominal breathing feature function.

In the following, the operation of each of the above steps of the method for extracting the feature of an abdominal breathing will be described in detail, in accompanied with figures.

Figure 2:
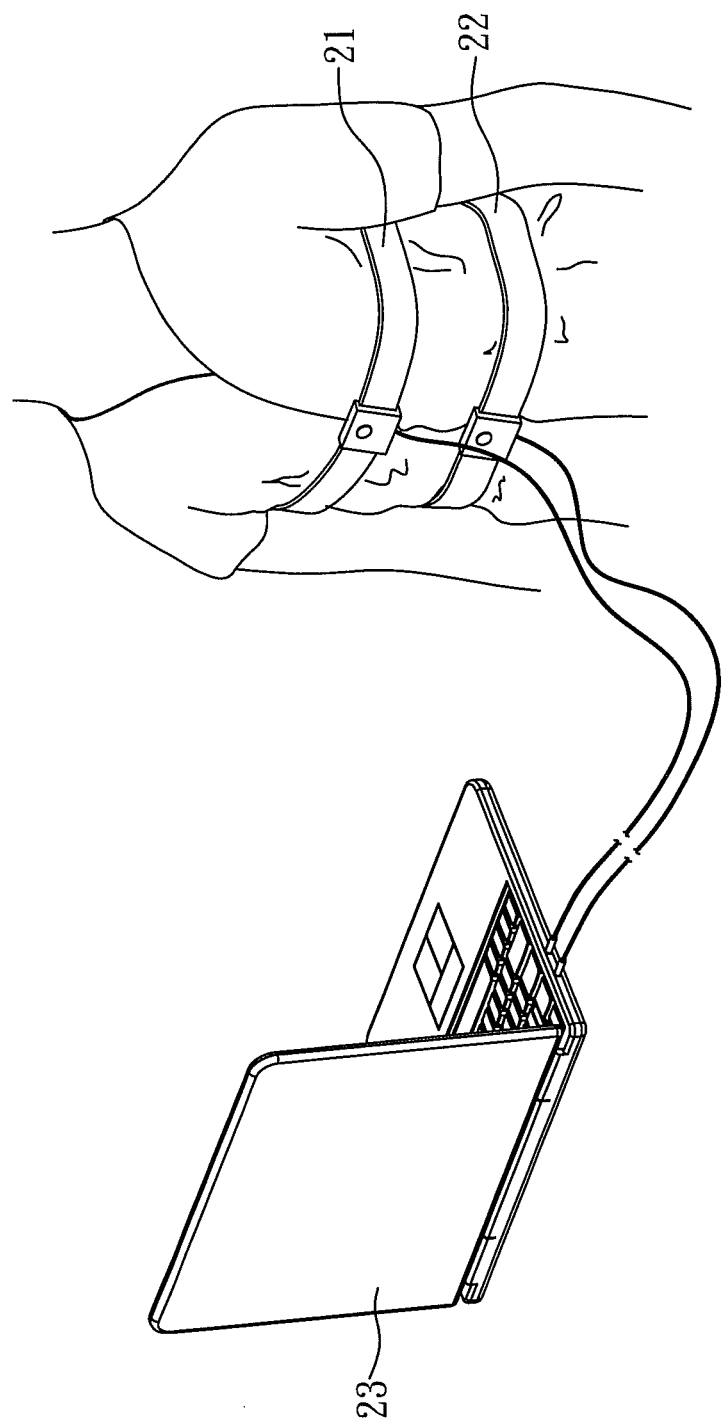
FIG. 2 is perspective view of an abdominal breathing feature extracting system.

Please refer to FIG. 2, which is a perspective view of an abdominal breathing feature extracting system. A person, whose abdominal breathing features are going to be extracted, wears two belts 21, 22, around his/her chest and abdominal, respectively. Then, the person executes abdominal breathing and/or thoracic breathing on his/her will, until be further instructed.

In the period of time when the method for extracting the feature of an abdominal breathing is executed, both of the displacement of the chest and the displacement of the abdominal of the person are acquired by the two belts 21, 22, respectively and simultaneously. The two belts 21, 22 convert the displacements into corresponding electronic signals, by means of using a PZT element. Once the electronic signals are obtained, which will be called as the abdominal breathing signals, are transmitted to a computer and/or portable devices 23, through any kind of possible signal transmission means, such as wire connection, for example, cables, or wireless connection. The computer and/or portable devices 23 store a program corresponding to the method for extracting the feature of an abdominal breathing according to first embodiment of the present invention, in the storage unit thereof.

Once the computer and/or portable devices 23 of the abdominal breathing feature extracting system receives the abdominal breathing signals, which is the step (A) of the method for extracting the feature of an abdominal breathing according to first embodiment of the present invention, the step (B) will be executed immediately. As shown in FIG. 1, in the step (B), an empirical mode decomposition process is executed on the acquired abdominal breathing signals, for computing a plurality of intrinsic mode functions of each of the abdominal breathing signals.

In the present embodiment, there are 2 breathing signals being acquired by the two belts 21, 22, while the person executing either of the thoracic breathing and the abdominal breathing. Then, all of these breathing signals are processed with the empirical mode decomposition process, which is shorten as the EMD process, for computing a plurality of intrinsic mode functions corresponding to each of these breathing signals, in the present embodiment, 2 of them.

Figure 3A:
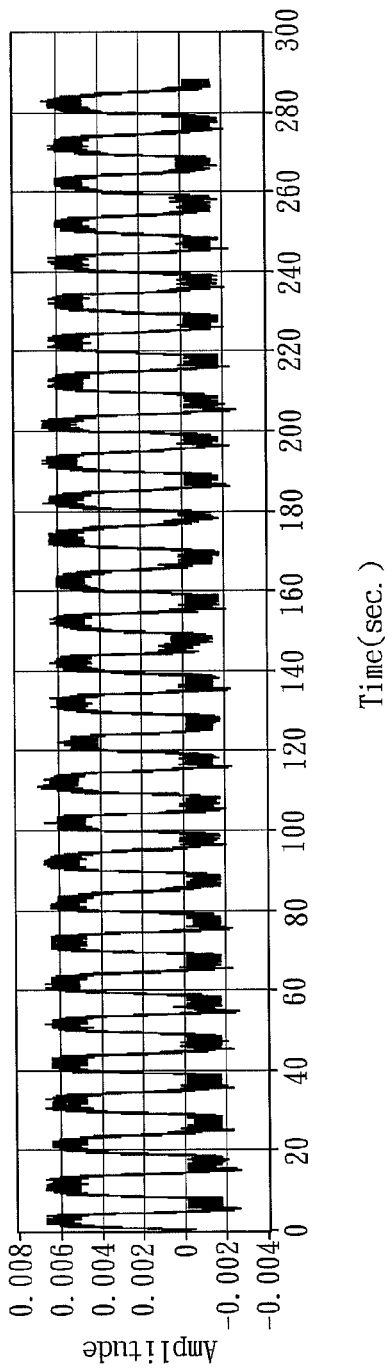
FIG. 3A displays the thoracic breathing signals acquired by a belt located on the chest of the person executing the thoracic breathing.

For example, as shown in FIG. 2, once the breathing signals acquired by the belt 21 having been received by the computer and/or portable devices 23, the computer and/or portable devices 23 execute the EMD process on the breathing signals, such as the one displayed in FIG. 3A, in order to obtain a plurality of intrinsic mode functions, so-called IMFs, corresponding to the thoracic breathing signals. In the case shown in FIG. 3A, there are 16 IMFs obtained, or "decomposed" from the thoracic breathing signals displayed in FIG. 3A.

Figure 3B:
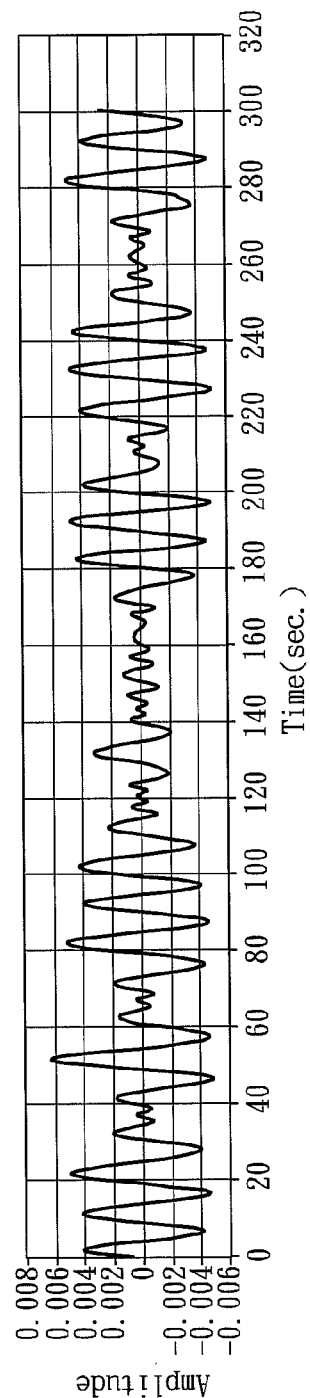
FIG. 3B displays one of the plurality of intrinsic mode functions corresponding to the thoracic breathing signals displayed in FIG. 3A.

After all of the IMFs corresponding to the thoracic breathing signals displayed in FIG. 3A is obtained, only the 11$^{th}$ of these IMFs is displayed in FIG. 3B, as an example. It should be noticed that, the selection of which of these IMFs to be displayed in FIG. 3B is arbitrary, and the selection of these IMFs should not limit the scope of the present invention.

In the following 8 figures, i.e. through FIG. 3A to FIG. 6B, the 4 breathing signals and the 4 IMFs obtained after the execution of the EMD process and the selection are respectively displayed. As described above, the thoracic breathing signals acquired by the belt 21 located on the chest of the person executing the thoracic breathing is displayed in FIG. 3A. The IMF obtained after the execution of the EMD process on the breathing signals displayed in FIG. 3A and the selection is displayed in FIG. 3B.

Figure 4A:
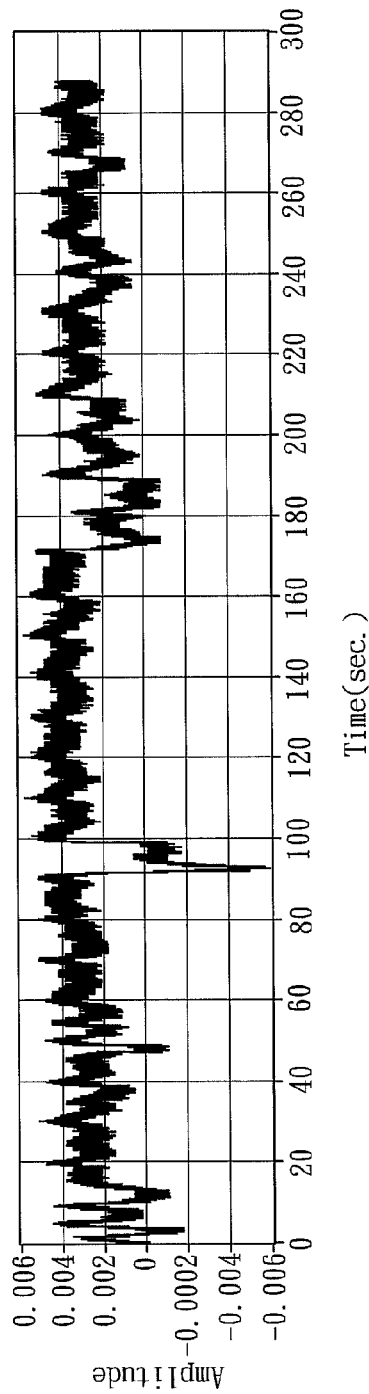
FIG. 4A displays the abdominal breathing signals acquired by a belt located on the abdominal of the person executing the thoracic breathing.
Figure 4B:
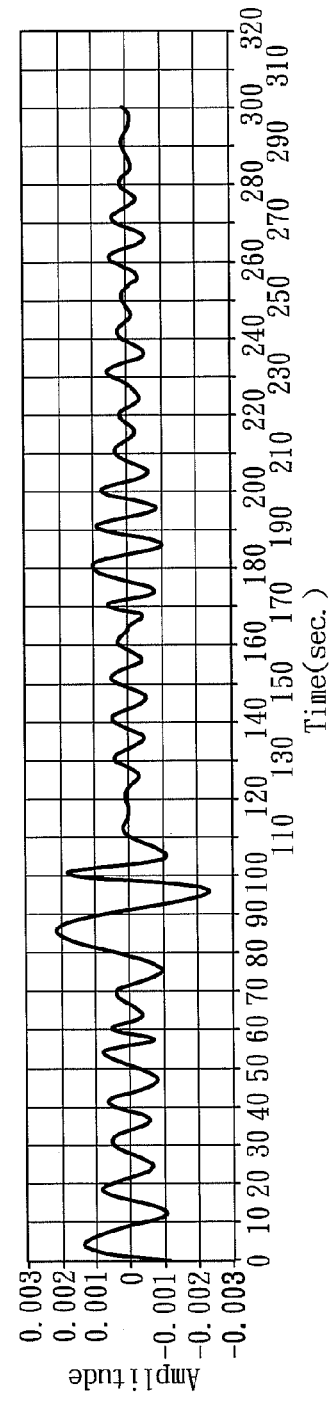
FIG. 4B displays one of the plurality of intrinsic mode functions corresponding to the abdominal breathing signals displayed in FIG. 4A.

In same manner, the abdominal breathing signals acquired by the belt 22 located on the abdominal of the person executing the thoracic breathing is displayed in FIG. 4A, while the IMF obtained after the execution of the EMD process on the breathing signals displayed in FIG. 4A and the selection is displayed in FIG. 4B. Besides, the thoracic breathing signals acquired by the belt 21 located on the chest of the person executing the abdominal breathing is displayed in FIG. 5A, while the IMF obtained after the execution of the EMD process on the breathing signals displayed in FIG. 5A and the selection is displayed in FIG. 5B.

Figure 6A:
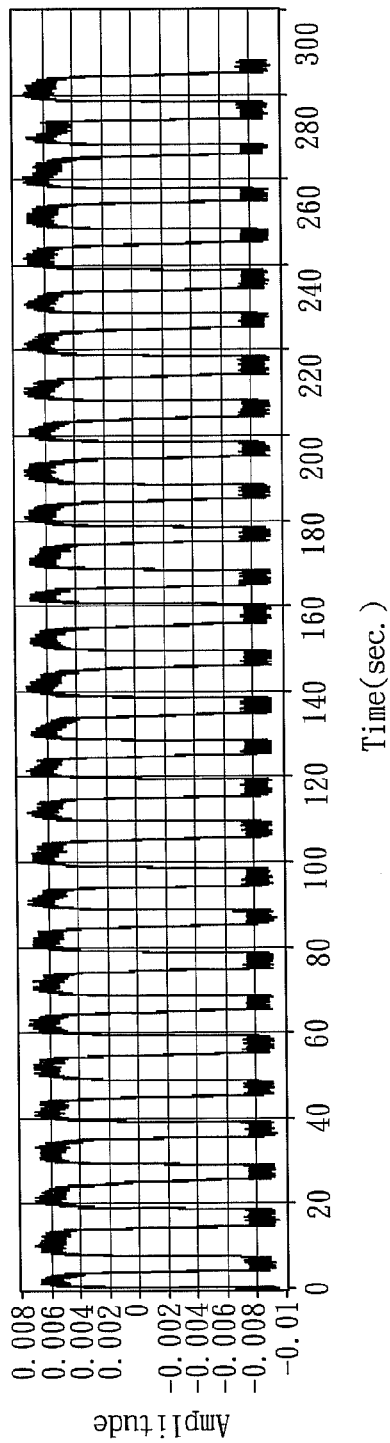
FIG. 6A displays the abdominal breathing signals acquired by a belt located on the abdominal of the person executing the abdominal breathing.
Figure 6B:
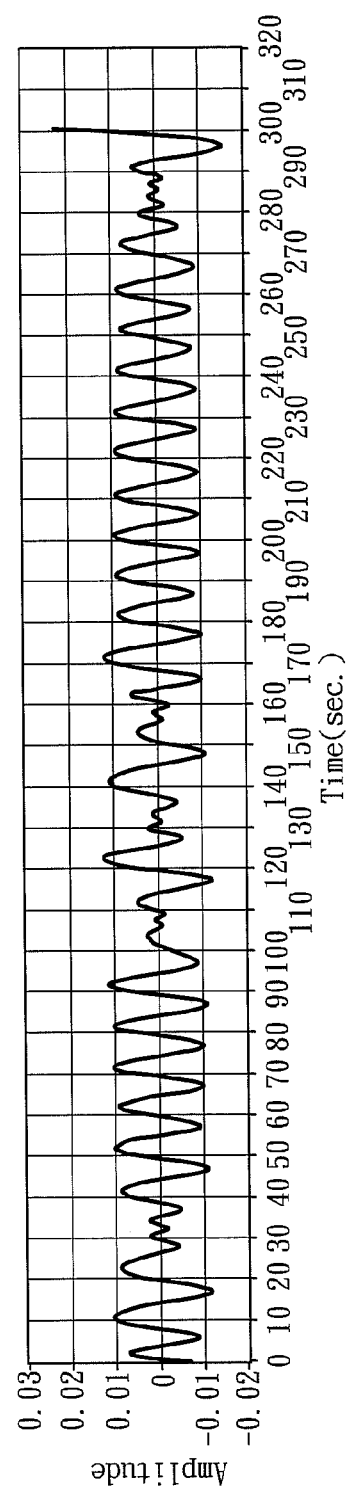
FIG. 6B displays one of the plurality of intrinsic mode functions corresponding to the abdominal breathing signals displayed in FIG. 6A.

In addition, the abdominal breathing signals extracted by the belt 22 located on the abdominal of the person executing the abdominal breathing is displayed in FIG. 6A, while the IMF obtained after the execution of the EMD process on the breathing signals displayed in FIG. 6A and the selection is displayed in FIG. 6B.

Since the execution of the EMD process on a signal, such as the breathing signal of the present invention, is well-known in the field, for example, the non-linear and non-stationary data processing field, detailed description regarding the execution of the EMD process will be omitted hereinafter.

After the plurality of IMFs of an abdominal breathing signal, such as the one displayed in FIG. 6A, being obtained, the step (C) of the method for extracting the feature of an abdominal breathing according to first embodiment of the present invention is executed. In the present embodiment, there are 16 IMFs corresponding to the abdominal breathing signals displayed in FIG. 6A. However, the number of the plurality of IMFs is not limited, there could be 1 to 16 IMFs corresponding to the abdominal breathing signals, depending on the characteristic of the IMFs. In addition, each of the plurality of IMFs has a characteristic frequency, and the values of the characteristic frequency of different IMFs are different from each other.

As shown in FIG. 1, in the step (C), an Euler angle function of each of the plurality of IMFs is computed basing on the plurality of IMFs and the results obtained after the execution of a Hilbert transform on the plurality of IMFs. In the present embodiment, since there are 16 IMFs, 16 results will be obtained after the execution of a Hilbert transform on these 16 IMFs, respectively. Therefore, 16 Euler angle functions will be obtained after the execution of the step (C).

Since the execution of the Hilbert transform on a function is well-known in the field, such as the signal processing field, detailed description regarding the execution of the Hilbert transform will be omitted hereinafter.

After executing the Hilbert transform on all of the 16 IMFs, 16 Euler angle functions will be obtained. In the present embodiment, the Euler angle function is a function describing the functional relation between the Euler angle and time in an Euler formula. The Euler formula can be represented as:

$$re^{j\theta} = r(\cos\theta + j\sin\theta) \quad \text{Formula (1)}$$

where, r represents the magnitude, and θ represents the Euler angle.

Therefore, since the Euler angle function is computed basing on an intrinsic mode function and the result obtained after the execution of a Hilbert transform on the IMFs, the Euler angle functions can be represented as:

$$r_a e^{j\theta_a} = \text{IMFs}_a + jH(\text{IMFs}_a) \quad \text{Formula (2)}$$

where, $r_a$ represents the magnitude of $a^{th}$ intrinsic mode function, $\theta_a$ represents the Euler angle of $a^{th}$ intrinsic mode function, and H represents the Hilbert transform.

As described above, 16 Euler angle functions are obtained after the execution of the step (C). Then, in the step (D) of the method for extracting the feature of an abdominal breathing according to first embodiment of the present invention, an instantaneous frequency function of each of the plurality of intrinsic mode function is computed, by taking the partial derivative of the Euler angle function of each of the plurality of intrinsic mode functions, with respect to time. The instantaneous frequency functions can be represented as:

$$\omega_a = \frac{d\theta_a}{dt} \quad \text{Formula (3)}$$

where, $\omega_a$ represents the instantaneous frequency functions of $a^{th}$ intrinsic mode function, and $\theta_a$ represents the Euler angle of $a^{th}$ intrinsic mode function.

As described above, since there are 16 IMFs corresponding to the breathing signals acquired by the belt 22 located on the abdominal of the person executing the abdominal breathing is displayed in FIG. 6A, 16 instantaneous frequency functions will be obtained after taking the partial derivative of the 16 Euler angle functions, with respect to time. Please refer to FIG. 7A to FIG. 7E, 5 of the 16 instantaneous frequency functions are displayed. It should be noticed that, the selection of these 5 instantaneous frequency functions to be displayed in these 5 figures is arbitrary, and the selection of these instantaneous frequency functions should not limit the scope of the present invention.

After all of these instantaneous frequency functions have been obtained, a plurality of maximum values of each of these instantaneous frequency functions, in the present embodiment, 16 of them, is extracted. Besides, as can be seen in these 5 figures, the plurality of maximum values of each of these 5 instantaneous frequency functions is local maximum values.

At last, in the step (E) of the method for extracting the feature of an abdominal breathing according to first embodiment of the present invention, the plurality of maximum values of each of the plurality of instantaneous frequency functions is compared with a zero-point threshold region, respectively, according to a pre-determined sequence. Besides, in the present embodiment, the pre-determined sequence is a sequence staring from the IMFs having a higher characteristic frequency value thereof, and terminating with the IMFs having a lower characteristic frequency value. In other words, the plurality of instantaneous frequency functions is sequenced, according to the characteristic frequency value of the IMFs corresponding thereto.

Figure 7A:
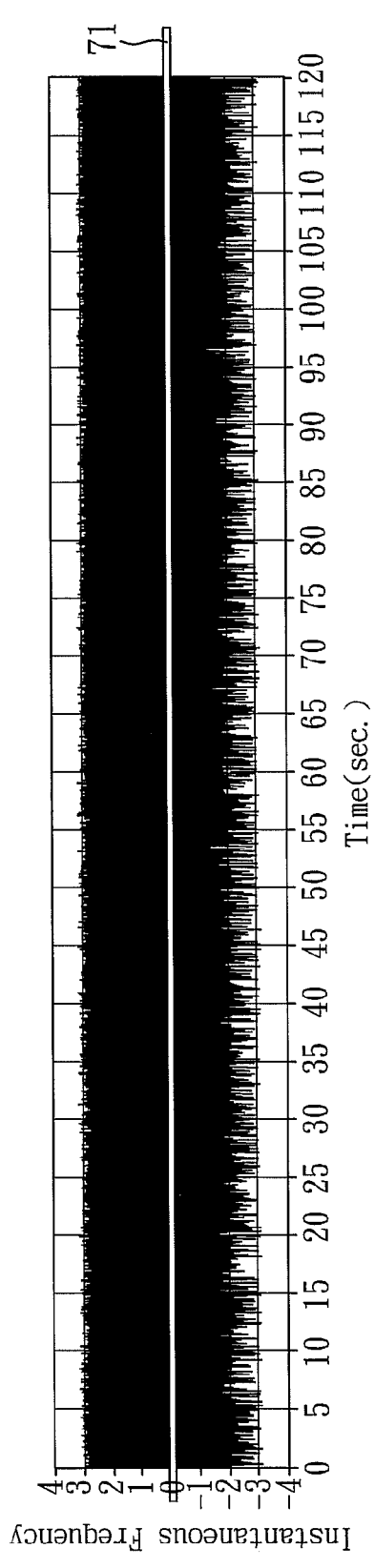
FIG. 7A to FIG. 7E display 5 instantaneous frequency functions, of 5 of the plurality of intrinsic mode functions corresponding to the abdominal breathing signals displayed in FIG. 6A.

As a result, in the present embodiment, the plurality of maximum values of the instantaneous frequency function, corresponding to the IMFs having a highest characteristic frequency value, is compared with a zero-point threshold region first, i.e. the instantaneous frequency function displayed in FIG. 7A.

As shown in FIG. 7A, the zero-point threshold region 71 is a region where the value of the instantaneous frequency function is between −0.5 and 0.5. In addition, as the zero-point threshold region 71 is between −0.5 and 0.5, the zero-point threshold region 71 is also called as the zero-point threshold ±0.5 region. As clearly shown in FIG. 7A, most of the plurality of maximum values of the instantaneous frequency function is higher than the top-limit of the zero-point threshold region 71. That is, the result that all of the plurality of maximum values of the instantaneous frequency function falling into the zero-point threshold region cannot be obtained.

Figure 7B:
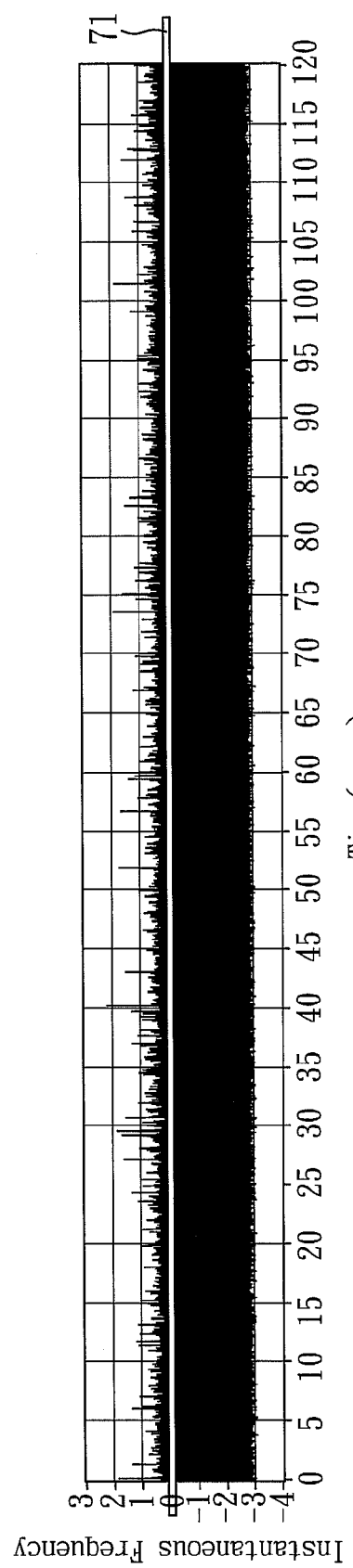

Then, turning to the next instantaneous frequency function in the pre-determined sequence, such as the one displayed in FIG. 7B. As clearly shown in the figure, some of the plurality of maximum values of the instantaneous frequency function is higher than the top-limit of the zero-point threshold region 71. That is, the result that all of the plurality of maximum values of the instantaneous frequency function falling into the zero-point threshold region cannot be obtained.

Figure 7C:
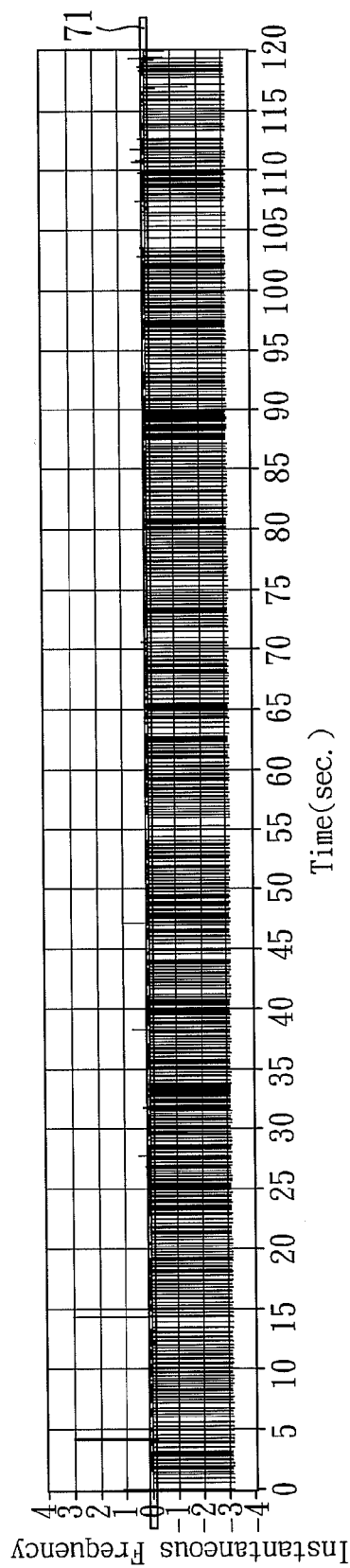

Next, in the same manner, turn to the next instantaneous frequency function in the pre-determined sequence, such as the one displayed in FIG. 7C. As clearly shown in the figure, the highest one of the plurality of maximum values of the instantaneous frequency function, i.e. the global maximum value, is higher than the top-limit of the zero-point threshold region 71. That is, the result that all of the plurality of maximum values of the instantaneous frequency function falling into the zero-point threshold region cannot be obtained.

Figure 7D:
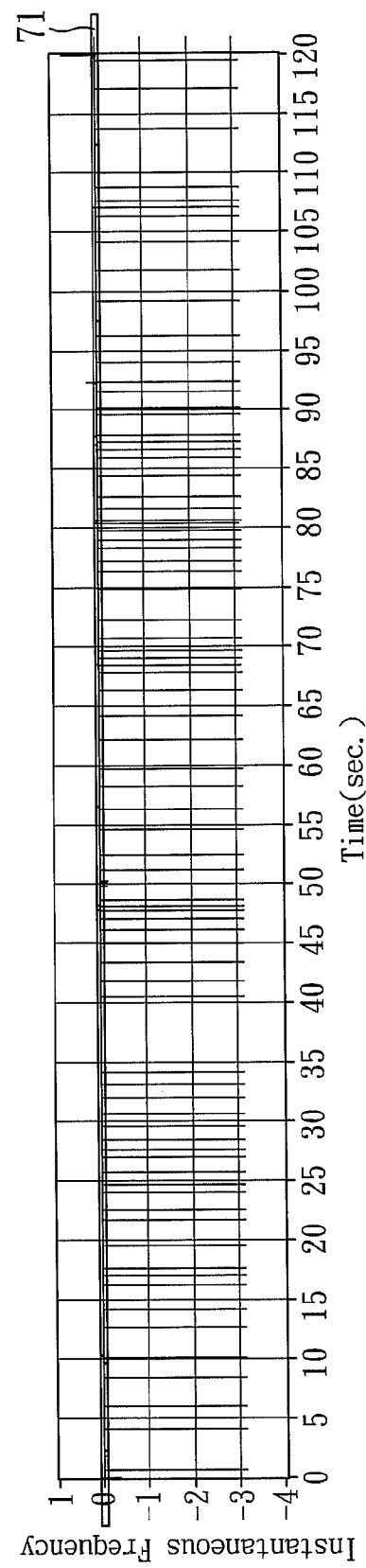

Next, in the same manner, turn to the next instantaneous frequency function in the pre-determined sequence, such as the one displayed in FIG. 7D. As clearly shown in the figure, the highest one of the plurality of maximum values of the instantaneous frequency function, i.e. the global maximum value raised around 93 seconds, is higher than the top-limit of the zero-point threshold region 71. That is, the result that all of the plurality of maximum values of the instantaneous frequency function falling into the zero-point threshold region cannot be obtained.

Figure 7E:
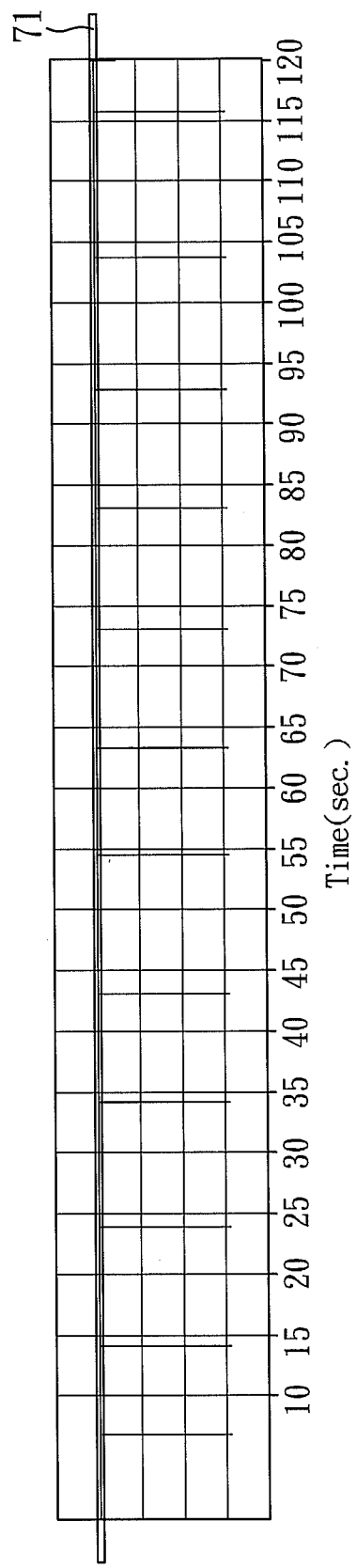

However, in the next instantaneous frequency function in the pre-determined sequence, such as the one displayed in FIG. 7E, the highest one of the plurality of maximum values of the instantaneous frequency function is lower than the top-limit of the zero-point threshold region 71, and the lowest of the plurality of maximum values of the instantaneous frequency function is higher than the bottom-limit of the zero-point threshold region 71. That is, the result that all of the plurality of maximum values of the instantaneous frequency function falling into the zero-point threshold region is obtained.

At this time, i.e. when a result that all of the plurality of maximum values of one of the plurality of instantaneous frequency functions falling into the zero-point threshold region is obtained, the instantaneous frequency function having the plurality of maximum values is defined as an abdominal breathing feature function. In this embodiment, the instantaneous frequency function displayed in FIG. 7E is defined as an abdominal breathing feature function, corresponding to the abdominal breathing signals displayed in FIG. 6A. Moreover, in the present embodiment, the distribution of the plurality of minimum values of the abdominal breathing feature function in the time dimension is the frequency of the abdominal breathing.

Figure 5A:
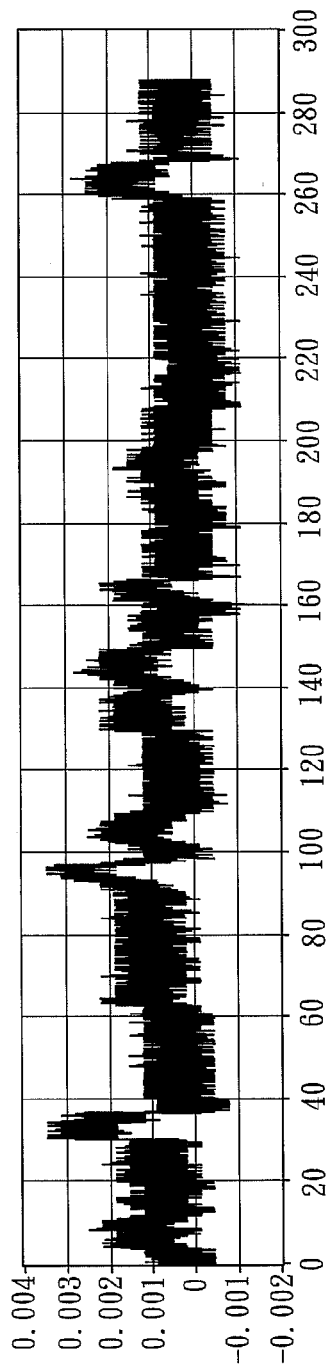
FIG. 5A displays the thoracic breathing signals acquired by a belt located on the chest of the person executing the abdominal breathing.
Figure 5B:
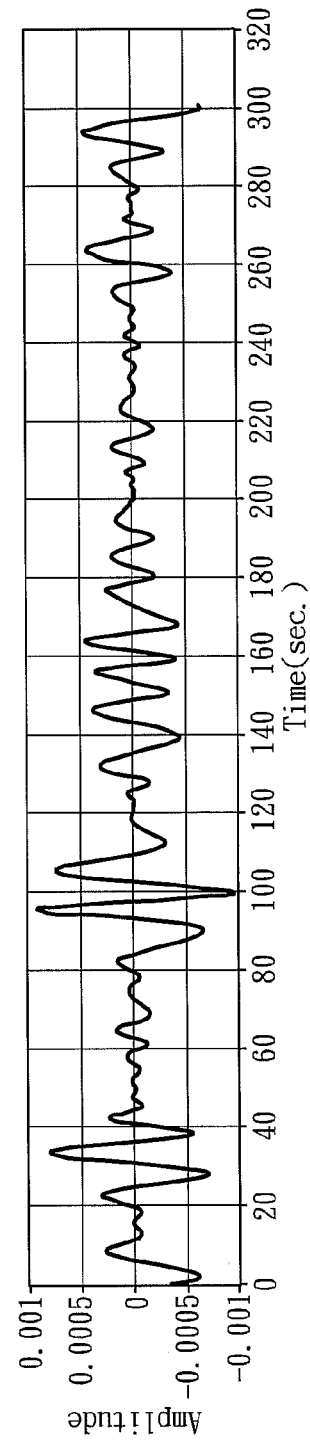
FIG. 5B displays one of the plurality of intrinsic mode functions corresponding to the thoracic breathing signals displayed in FIG. 5A.

It should be noticed that, by executing the method for extracting the feature of an abdominal breathing according to first embodiment of the present invention, all of the abdominal breathing feature functions corresponding to other abdominal breathing signals can be respectively obtained, such as the abdominal breathing signal displayed in FIG. 5A, the abdominal breathing signal displayed in FIG. 6A.

Figure 8:
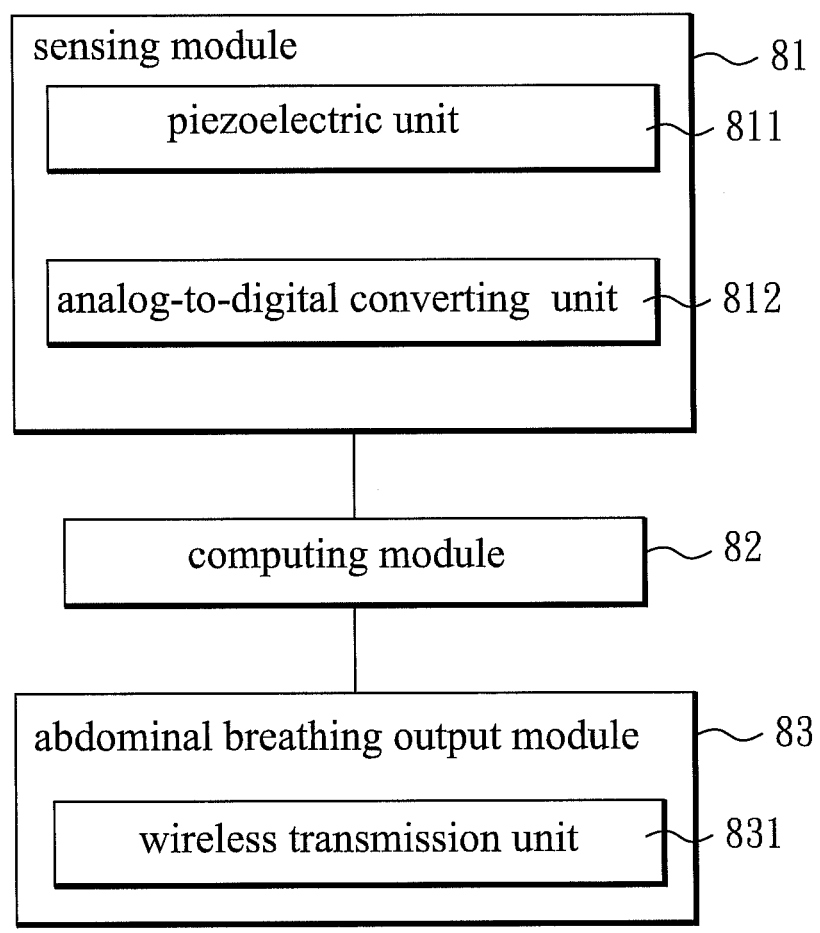
FIG. 8 is a perspective view of the abdominal breathing feature extracting system according to second embodiment of the present invention.

Please refer to FIG. 8, which is a perspective view of the abdominal breathing feature extracting system according to second embodiment of the present invention. As shown in the figure, the abdominal breathing feature extracting system according to second embodiment of the present invention comprises: a sensing module 81, a computing module 82 coupled with the sensing module 81, and an abdominal breathing feature output module 83 coupled with the computing module 82. Wherein, the sensing module 81 is used for sensing an abdominal breathing signal, while the computing module 82 is used for extracting an abdominal breathing feature function. In addition, the abdominal breathing feature output module 83 is used for outputting the abdominal breathing feature function.

Figure 9:
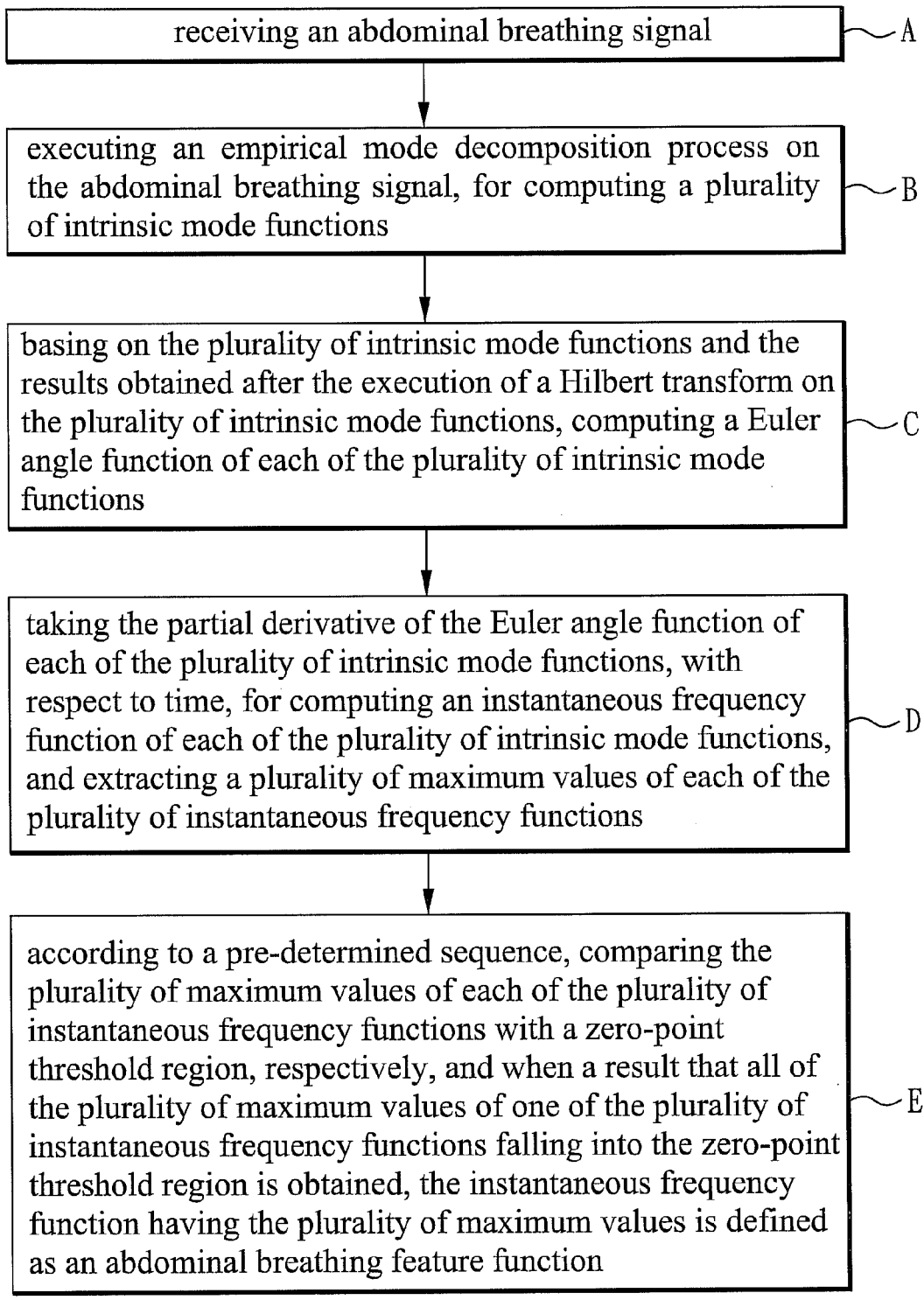
FIG. 9 is a flowchart of the method for extracting the feature of an abdominal breathing executed by the computing module of the abdominal breathing feature extracting system according to second embodiment of the present invention.

In addition, the computing module 82 extracts the abdominal breathing feature function from the abdominal breathing signal, by means of executing an abdominal breathing feature extracting method. As shown in FIG. 9, the abdominal breathing feature extracting method comprises the following steps of:

(A) receiving the abdominal breathing signal;
(B) executing an empirical mode decomposition process on the abdominal breathing signal, for computing a plurality of intrinsic mode functions;
(C) basing on the plurality of intrinsic mode functions and the results obtained after the execution of a Hilbert transform on the plurality of intrinsic mode functions, computing an Euler angle function of each of the plurality of intrinsic mode functions;
(D) taking the partial derivative of the Euler angle function of each of the plurality of intrinsic mode functions, with respect to time, for computing an instantaneous frequency function of each of the plurality of intrinsic mode functions, and extracting a plurality of maximum values of each of the plurality of instantaneous frequency functions; and
(E) according to a pre-determined sequence, comparing the plurality of maximum values of each of the plurality of instantaneous frequency functions with a zero-point threshold region, respectively, and when a result that all of the plurality of maximum values of one of the plurality of instantaneous frequency functions falling into the zero-point threshold region is obtained, the instantaneous frequency function having the plurality of maximum values is defined as the abdominal breathing feature function.

In the present embodiment, the sensing module 81 of the abdominal breathing feature extracting system according to second embodiment of the present invention is integrated to a belt. For example, a belt for a person to wear on his/her body, preferably around the abdominal. In addition, as shown in FIG. 8, the sensing modules 81 includes a piezoelectric unit 811 for extracting the displacement of the person's body, and an analog-to-digital converting unit 812 electrically connected with the piezoelectric unit, in order to convert the analog signal output from the piezoelectric unit into a corresponding digital signal. Besides, for minimizing the size and weight of the sensing module, the sensing module is a system on chip (SoC).

In addition, as shown in FIG. 8, the abdominal breathing feature output module 83 includes a wireless transmission unit 831, for outputting the abdominal breathing feature function to a remote server (not shown in the figure) through a wireless connection, such as the 3G or the WiFi technology.

Since the abdominal breathing feature extracting method executed by the computing module 82 of the abdominal breathing feature extracting system according to second embodiment of the present invention is the same abdominal breathing feature extracting method described in the first embodiment of the present invention, detailed description regarding the operation of the abdominal breathing feature extracting method is omitted hereinafter, for simplify the description of the present embodiment.

Although the present invention has been explained in relation to its preferred embodiment, it is to be understood that many other possible modifications and variations can be made without departing from the spirit and scope of the invention as hereinafter claimed.

What is claimed is:

1. A method for extracting the feature of an abdominal breathing, comprising the following steps of:
   receiving an abdominal breathing signal;
   executing, using a computer, an empirical mode decomposition process on the abdominal breathing signal, for computing a plurality of intrinsic mode functions;
   executing, using the computer, a Hilbert transform on the plurality of intrinsic mode functions;
   computing an Euler angle function of each of the plurality of intrinsic mode functions based on the plurality of intrinsic mode functions and the results obtained after the execution of the Hilbert transform on the plurality of intrinsic mode functions;
   computing an instantaneous frequency function of each of the plurality of intrinsic mode functions by taking the partial derivative of the Euler angle function of each of the plurality of intrinsic mode functions, with respect to time; and
   extracting, using the computer, a plurality of maximum values of each of the plurality of instantaneous frequency functions; and
   comparing, using the computer, the plurality of maximum values of each of the plurality of instantaneous frequency functions with a zero-point threshold region, respectively, according to a pre-determined sequence; and
   defining an abdominal breathing feature function as the instantaneous frequency function having the plurality of maximum values when a result that all of the plurality of maximum values of one of the plurality of instantaneous frequency functions falling into the zero-point threshold region is obtained.

2. The method as claimed in claim 1, wherein the Euler angle function is a function describing the functional relation between the Euler angle and time in an Euler formula, and the Euler formula is represented as:

$$re = r(\cos\theta + j\sin\theta)$$

where, r represents the magnitude, and $\theta$ represents the Euler angle.

3. The method as claimed in claim 1, wherein the plurality of maximum values of each of the plurality of instantaneous frequency functions is local maximum values.

4. The method as claimed in claim 1, wherein the number of the plurality of intrinsic mode functions is between 1 and 16, and each of the plurality of intrinsic mode functions has a characteristic frequency, and the values of the characteristic frequency of different intrinsic mode functions are different from each other.

5. The method as claimed in claim 4, wherein the pre-determined sequence is a sequence staring from the intrinsic mode function having a higher characteristic frequency value thereof, and terminating with the intrinsic mode function having a lower characteristic frequency value.

6. The method as claimed in claim 1, wherein the zero-point threshold region is a region where the value of the instantaneous frequency function is between −0.5 and 0.5.

7. The method as claimed in claim 1, wherein the distribution of the plurality of minimum values of the abdominal breathing feature function in the time dimension is the frequency of the abdominal breathing.

8. An abdominal breathing feature extracting system, comprising:
   a sensor, for sensing an abdominal breathing signal;
   a computer, coupled with the sensor, for extracting an abdominal breathing feature function; and
   an output unit, coupled with the computer, for outputting the abdominal breathing feature function;
   wherein, the computer extracts the abdominal breathing feature function from the abdominal breathing signal by executing an abdominal breathing feature extracting method, and the abdominal breathing feature extracting method comprises the following steps of:
   receiving the abdominal breathing signal;
   executing an empirical mode decomposition process on the abdominal breathing signal, for computing a plurality of intrinsic mode functions;
   executing a Hilbert transform on the plurality of intrinsic mode functions;
   computing an Euler angle function of each of the plurality of intrinsic mode functions based on the plurality of intrinsic mode functions and the results obtained after the execution of the Hilbert transform on the plurality of intrinsic mode functions;
   computing an instantaneous frequency function of each of the plurality of intrinsic mode functions by taking the partial derivative of the Euler angle function of each of the plurality of intrinsic mode functions, with respect to time; and
   extracting a plurality of maximum values of each of the plurality of instantaneous frequency functions; and
   comparing the plurality of maximum values of each of the plurality of instantaneous frequency functions with a zero-point threshold region, respectively, according to a pre-determined sequence; and
   defining an abdominal breathing feature function as the instantaneous frequency function having the plurality of maximum values when a result that all of the plurality of maximum values of one of the plurality of instantaneous frequency functions falling into the zero-point threshold region is obtained.

9. The system as claimed in claim 8, wherein the sensing module is integrated to a belt, and the sensing module includes a piezoelectric unit and an analog-to-digital converting unit.

10. The system as claimed in claim 8, wherein the sensing module is a system on chip.

11. The system as claimed in claim 8, wherein the abdominal breathing feature output module includes a wireless transmission unit.

12. The system as claimed in claim 8, wherein the Euler angle function is a function describing the functional relation between the Euler angle and time in an Euler formula, and the Euler formula is represented as:

$$re^{j\theta} = r(\cos\theta + j\sin\theta)$$

where, r represents the magnitude, and θ represents the Euler angle.

13. The system as claimed in claim 8, wherein the number of the plurality of intrinsic mode functions is between 1 and 16, and each of the plurality of intrinsic mode functions has a characteristic frequency, and the values of the characteristic frequency of different intrinsic mode functions are different from each other.

14. The system as claimed in claim 8, wherein the predetermined sequence is a sequence staring from the intrinsic mode function having a higher characteristic frequency value thereof, and terminating with the intrinsic mode function having a lower characteristic frequency value.

15. The system as claimed in claim 8, wherein the zero-point threshold region is a region where the value of the instantaneous frequency function is between −0.5 and 0.5.

16. The system as claimed in claim 8, wherein the distribution of the plurality of minimum values of the abdominal breathing feature function in the time dimension is the frequency of the abdominal breathing.

\* \* \* \* \*